United States Patent [19]

Stepan-Sarkissian et al.

[11] Patent Number: 5,670,357
[45] Date of Patent: Sep. 23, 1997

[54] PEROXIDASE PRODUCED BY PLANT CELL CULTURES

[75] Inventors: Gagik Stepan-Sarkissian, Courbevoie, France; Debbie Grey, Derbyshire, United Kingdom; Margaret Elizabeth Spencer, Sheffield, United Kingdom; Angela Marian Stafford, Castleton, United Kingdom; Sean Michael Vincent Ashton, Sheffield, United Kingdom; Sandra Jane Scollick, Barnsley, United Kingdom

[73] Assignee: Phytera, Inc., Worcester, Mass.

[21] Appl. No.: 190,102

[22] PCT Filed: Sep. 16, 1992

[86] PCT No.: PCT/GB92/01700

§ 371 Date: Sep. 19, 1994

§ 102(e) Date: Sep. 19, 1994

[87] PCT Pub. No.: WO93/06212

PCT Pub. Date: Apr. 1, 1993

[30] Foreign Application Priority Data

Sep. 16, 1991 [GB] United Kingdom ............... 9119717

[51] Int. Cl.$^6$ ........................................ C12N 9/08
[52] U.S. Cl. ............... 435/192; 435/240.54; 435/240.46
[58] Field of Search ................. 435/192, 240.54, 435/240.46

[56] References Cited

FOREIGN PATENT DOCUMENTS

| 59-028473 | 2/1984 | Japan . |
|---|---|---|
| 01222776 | 9/1989 | Japan . |
| 01222777 | 9/1989 | Japan . |
| 01222778 | 9/1989 | Japan . |
| 9110729 | 7/1991 | WIPO . |

OTHER PUBLICATIONS

Shetty et al., Applied Biochemistry & Biotechnol., vol. 2425, 1990, 213–221.
J. Dubois et al., 20(2), 107–113, 1978, Biologia Plantarium (Prahg).
Kaosivi et al., My Cologia, 72(5), 988–1000, 1980.
Atkinson et al., Euphytica, 35(1986), 741–50.
Forage A. J., Process Biochemistry, 1979 pp. 8–9 and 30.
Yamada et al., J. Chem. Tech. Biotechnol., 1987, vol. 38, pp. 31–39.
Callebaut et al, (II) Biotechnol Lett., 12(3), 215–218, 1990.
Callebaut et al, (I) Plant Cell Rep., 7(3), 162–165, 1988.
Balasimha et al., Indian J. Exp. Biol., 21(2):65–68 (1983).
Gamborg et al., Exp. Cell Res., 50:151–158 (1968).
Grey, Methods in Molecular Biology, Plant Cell and Tissue Culture, Clifton, New Jersey, Humana Press, vol. 6, pp. 555–562.
Hepler et al., Canadian J. Botony, 50(5):977–983 (1972).
Legrand et al., Comptes Rendus Hebdomadaires Des Seances de L'Academie Des Sciences, Series D: Sciences Naturelles, 285, 661–664 (1977).
Murashige et al., Physiol. Plant., 15:473–497 (1962).
Schripsema et al., Plant Cell Tissue Organ Cult., 22:55–64 (1990).
Stepan–Sarkissian et al., Methods in Molecular Biology, Plant Cell and Tissue Culture, Clifton, New Jersey, Humana Press, vol. 6, pp. 13–27 (1990).

Primary Examiner—Irene Marx
Attorney, Agent, or Firm—Fish & Richardson P.C.

[57] ABSTRACT

A process for the production of peroxidase enzyme comprising an undifferentiated liquid suspension culture of peroxidase-producing plant cells from a plant of the species Theobroma cacao, Coleus blumei, and Silene alba, wherein the culture medium contains a carbohydrate waste material, and peroxidase enzymes derived therefrom.

3 Claims, 13 Drawing Sheets

Key

1. Pooled, concentrated sample, prior to separation
2. Column fraction 27 ⎤
3. " " 28 ⎬ PT-S1
4. " " 29 ⎦
5. " " 31 ⎤
6. " " 32 ⎬ PT-S2
7. " " 33 ⎦
8. " " 36 ⎤
9. " " 37 ⎬ PT-S3
10. " " 38 ⎦
11. SDS 7 molecular weight markers Key 1. SDS 7 molecular weight markers
2. Pooled, concentrated sample, prior to separation
3. Column fraction 19
4. " " 20
5. " " 21
6. " " 22
7. " " 23
8. " " 24
9. " " 25
10. " " 26
11. SDS 7 molecular weight markers

PEROXIDASE PRODUCED BY PLANT CELL CULTURES

This application was filed under 35 U.S.C. 371 as the national phase of PCT16892/01700, filed Sep. 16, 1992.

FIELD OF INVENTION

This invention relates to a process for the production of peroxidase enzymes from plant cell cultures, and specific isoenzymes isolated therefrom.

BACKGROUND AND PRIOR ART

Peroxidase enzymes catalyse a host of reactions in which hydrogen peroxide is a specific oxidising agent and a wide range of substrates act as electron donors. They are widely used as enzyme labelled reagents in diagnostic, e.g. ELISA, kits, and in other biologically based molecular detection systems, but also find utility in other industries, such as in paper recycling, chemical and waste water treatment, and in detergents and bleaching agents.

Peroxidase enzymes are widely distributed in nature and are produced by a wide variety of plant species. At the present time however, the chief commercial source is horseradish. In the commercial production of horseradish peroxidase (HRP) the horseradish roots are harvested and the sprouted roots are minced mechanically in water to form a starting material. From this, peroxidase is purified by a series of ammonium sulphate and ethanol precipitations. To obtain high purity enzyme, conventional chromatographic techniques are employed. Unfortunately, this process leads to large quantities of waste tissue and problems arise with dispersing of waste. Not only this but there is a significant irreversible loss of enzyme activity resulting from the precipitations with ethanol and ammonium sulphate which are used to extract the enzyme from the tissue.

In International Patent Application, Publication No. WO91/10729, plant cell suspension cultures are described which produce an extra-cellular peroxidase in high yield and which therefore provide a convenient source of peroxidase which is not subject to the foregoing recovery problems. These are suspension cultures of peroxidase producing cells of plants of the genus *Acer*, and especially root cell cultures of *Acer pseudoplatanus*.

Various other sources have been suggested in the literature for the commercial production of peroxidase. For example, radish plant cell cultures have been suggested as a source of extra-cellular peroxidase (Plant Cell, Tissue and Organ Culture, 1989, 18:321–327) but the yields and specific activity of the product enzyme are low.

It has also been suggested that calli cultured from various plant species can be used as a source for the production of peroxidase, but callus culture is inherently incapable of large scale commercial production. Such suggestions are Contained in unexamined published Japanese Patent Applications:

JP-A-1222778 (source species: *Glycyrrhiza glabra* L.var, *Ipomea batatas* Lam. vat *deulis Makino, Stevia rebaudiana Bettoni,* and *Bupleurum falcatum* L.);

JP-A-1222777 (source species: *Zoysia japonica,* and *Zoysia macrostachchya*);

JP-A-1222776 (source species: *Trifolium repens* L., *Carica papaya* L., *Phellodendron amurense* Rupr., *Oenothera lamarchiana* Ser., *Scopolia japonica* Maxim, *Lithospermum erythrorhizon* Sieb et Zucc., *Glycine max* Merrill, and *Gynastema pentaphyllum Makino*);

JP-A-63233782 (source species: general);

JP-A-62138188 (source species: *Ipomea aquatica Forsk*).

Other items of background at1 include:

Applied Biochemistry and Biotechnology, 1990, Vol 24/25, pp 213–222, which discloses the correlation between extra-cellular peroxidase production and plant cell growth in plant cell cultures of *Artemesia annua, Coleus blumei, Pisum satiuum,* and *Salvia officinalis* and the consequential utility of extra-cellular peroxidase concentration in such cultures as an indicator of cell growth, but not as a commercial source of peroxidase enzymes;

Care Cacao The, 1985, 29(2), pp 113–120 which reports on the effects of fermentation on the activity of peroxidase and polyphenol-oxidase enzymes in the cocoa bean, but in no way suggests cell cultures of *T. cacao* as a commercial source of peroxidase;

Indian Journal Experimental Biology, 1983, Vol 21, pp 65–68 which reports on the role of o- and p-hydroxybenzoic acid (HBA) as synergists of indole-3-butyric acid (IBA) in the rooting of single node stem cuttings of *T. cacao,* and showed both an increase in rhizogenesis and peroxidase activity in stem cuttings treated with either or both HBA and IBA as compared with controls, and showed that increased peroxidase levels occurred in the treated cuttings prior to rooting, but dropped rapidly after root formation. This therefore was simply a study of the role of HBA and IBA in the rooting of *T. cacao* stem cuttings and the involvement of peroxidase enzymes in the process of rhizogenesis, with no suggestion of *T. cacao* cell cultures as a commercial source of peroxidase.

OBJECTS OF THE INVENTION

An object of the invention is to provide alternative sources of peroxidase enzymes.

A further object is to provide alternative sources for the commercial production of peroxidase enzymes by plant cell culture techniques.

A further object is to provide plant cell cultures capable of producing peroxidase enzymes in high yield in a culture medium, preferably, but not necessarily, as an extra-cellular rather than intra-cellular product, thus simplifying recovery of the enzyme from the culture medium.

A further object of the invention is to provide plant cell cultures capable of producing peroxidase enzymes showing exceptionally high levels of peroxidase activity.

A further object is to provide, in isolated form, novel peroxidase isoenzymes having activity levels substantially higher than that of HRPO.

These and other objects will become apparent from the following description.

SUMMARY OF THE INVENTION

In accordance with the present invention, other plant cell cultures have been discovered capable of producing high yields of peroxidase, in some cases intra-cellularly but, in the preferred cases extra-cellularly. These are plant cell cultures of: *Theobroma cacao* (cocoa) family: *Sterculiaceae Coleus blumei* family: *Labiatae* and *Silene alba* (white campion) family: *Caryophyllaceae* none of which are related to *Acer* (sycamore) species (family: *Aceraceae*) previously described or to any other known peroxidase yielding plant species.

BRIEF DESCRIPTION OF THE DRAWINGS

Data relating to the production of peroxidase enzymes by plant cell cultures according to this invention is presented in the accompanying drawings, in which.

DETAILED DESCRIPTION

Figure 1:
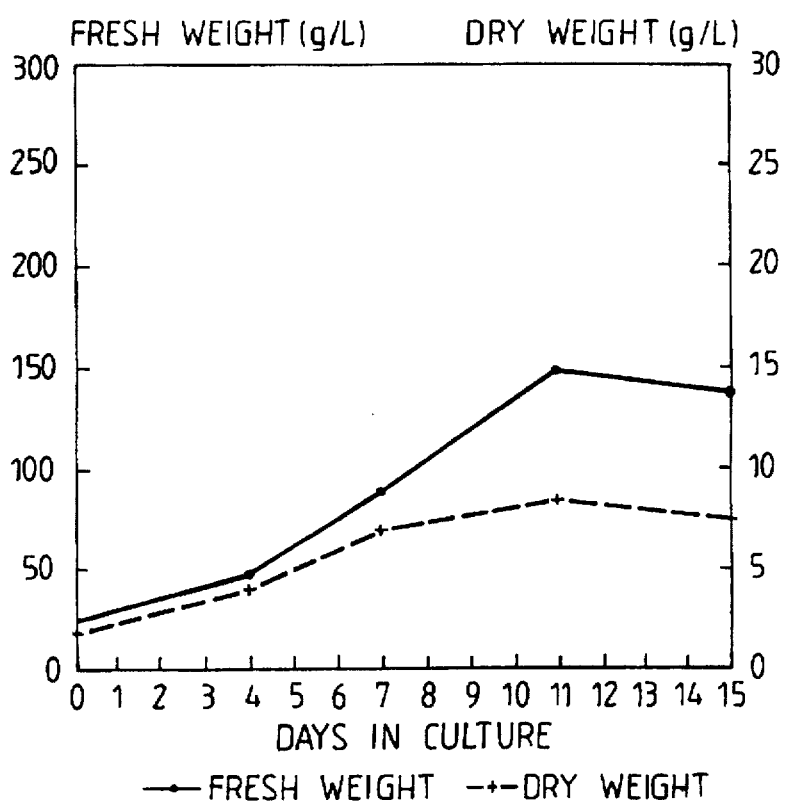
FIG. 1 shows the fresh and dry weights of *T. cacao* growth cycle, with glucose as the carbon source.

In accordance with the present invention, therefore, there is provided a process for the production of peroxidase enzyme which comprises establishing a plant cell culture of peroxidase producing cells from a plant of the species: *Theobroma cacao Coleus blumei* or *Silene alba* in suspension in a culture medium capable of supporting the growth of the peroxidase-producing plant cells, continuing the culture of said cells in suspension in the culture medium with the concomitant accumulation of extra-cellular and/or intra-cellular peroxidase, and recovering the accumulated peroxidase from the culture.

Preferably the cultures are established using pod tissue of *Theobroma cacao*, leaf tissue of *Coleus blumei* or epicotyl tissue of *Silene alba*.

Suspension cultures of *Theobroma cacao, Coleus blumei* and *Silene alba* can be established and maintained using conventional plant cell culture techniques and using media, such as Gamborg's B5 medium or a Murashige and Skoog (MS) medium containing a suitable carbon source, e.g. one or more of sucrose, glucose and fructose in an amount of from 1 to 15% by weight, preferably from about 2 to 5%, and the necessary phytohormones e.g. kinetin and 2,4-dichlorophenoxyacetic acid.

Generally the cultures are initiated on a first medium, e.g. on agar, and once established, are transferred by aseptic inoculation either directly into a suitable production medium, or possibly first into a maintenance medium to promote continued growth prior to inoculation in a production medium. Generally the production culture will be carried out on a batch basis, although semi-continuous or continuous culture techniques with periodic or continuous withdrawal of culture medium and/or cells for recovery of the product peroxidase, may be used.

As the production medium for the plant cell culture there may be used any suitable culture medium for plant cell cultures, e.g. Gamborg's B5 medium or Hurashige and Skoog (MS) medium containing suitable carbon source, e.g. one or more of glucose, sucrose and fructose in an amount of from 1 to 15% by weight, preferably from about 2 to 5%, and most preferably about 3%, and the necessary phytohormones, e.g. 2,4-dichlorophenoxyacetic acid and kinetin and preferably a culture medium specifically formulated as a production medium rather than as a maintenance medium, the formulation of such production media being well established in the art.

A characteristic feature of the plant cell cultures used in accordance with the present invention is that it has been found possible to use carbohydrate waste materials containing glucose and/or sucrose and/or fructose, such as are produced in large amounts in the confectionery industry, as the carbon source in the culture medium, rather than the customarily used refined glucose and/or sucrose. Glucose and/or Sucrose and/or fructose containing wastes produced the confectionery industry, e.g. floor sweepings, misshapen moulded confectioneries and discontinued lines, present a substantial disposal problem in the confectionery industry since it is usually not economic to reprocess the waste, and simply dumping the waste presents environmental problems. In accordance with the present invention, it has been found that such wastes provide an inexpensive source of glucose and/or sucrose and/or fructose for the plant cell cultures and which can be supplied simply by extracting the waste confectionery with water and feeding the crude extract, without further purification or refinement, to the culture medium, the plant cell culture being remarkably tolerant to the other water soluble ingredients, dyes etc. in the waste confectionery.

Generally the production culture will be carried out under aerobic conditions, usually at a pH in the range 5.6 to 5.8 and at a temperature of about 25° C., and although the optimum conditions for each, species differ, these can be established without any difficulty by any person with experience and skill in the field of plant cell culture technology. For example, by aseptically taking small culture samples from the culture vessel at regular intervals, and monitoring fresh and dry weight measurements, cell viability, culture pH and peroxidase activity, it is possible to determine an optimum culture time and optimum conditions for the efficient production of peroxidase.

Depending upon the species, optimum production of peroxidase occurs after about 8 to 15 days.

For small scale experimental work the cultures are sub-cultured by weight, e.g. 3 g fresh weight per 100 mL medium. For intermediate scale cultures up to 10L, two liters of 14 day old cultures can be used an inoculum in 8L of fresh medium in a reaction vessel equipped with a stirrer and aerated with a compressed air feed. Larger scale cultures can be conducted in a 30L, airlift fermenter aerated with compressed air for example at the rate of about 6L/min.

Extraction of peroxidase from the culture medium is achieved by conventional downstream processing techniques, which may or may not include disruption of the cells, preferably after separation from the culture liquor to enable recovery of intra-cellular as well as extra-cellular peroxidase. For many commercial purposes it will be sufficient simply to concentrate the culture liquor following separation to provide a crude, and possibly dried peroxidase containing extract. For example, after separating cell solids, the liquor may be concentrated by ultrafiltration techniques such as successive passage through a first filter with a molecular weight cut-off at about 100,000 followed by a second filter with a cut-off at about 20,000. If further purification is necessary, this can be achieved by conventional chromatography purification procedures.

Where intra-cellular peroxidase is to be recovered as the process product instead of or as well as extra-cellular peroxidase this may be recovered by separating the cultured plant cell tissue from the culture medium to provide a supernatant liquor containing the accumulated extra-cellular peroxidase, recovering the extra-cellular peroxidase, from the supernatant liquor and further processing the separated plant cell tissue to recover intra-cellular peroxidase as a separate product.

Preferably the intra-cellular peroxidase is recovered from the separated plant cell tissue by disrupting the cells in the separated plant cell tissue, extracting the intra-cellular peroxidase from the disrupted plant cells by extraction with ethanol and precipitating the extracted intra-cellular peroxidase with ammonium sulphate.

In accordance with a specific aspect of the invention, the peroxidase isoenzymes are provided in substantially pure form, i.e. purified to the level of a single band on SDS-PAGE gel, all showing substantially higher levels of peroxidase activity than HRP. These are A) the peroxidase isoenzyme PT-S3 having the following characteristics:

| Natural Source: | Theobroma cacao |
|---|---|
| Location: | Extra-cellular |
| Mol. wt: | circa 33 kD |
| Optimum pH: | 4.5 |
| Stability: | >33% activity retained after 1 year at 4° C. in sodium acetate or phosphate buffer |
| Haem Peak $\lambda_{max}$: | 403 nm |
| $R_2$: | 2.05 |
| pI: | >10 |
| Highest Specific Activity (ABTS): | 12046 U/mg |
| Highest Specific Activity (Guaiacol): | 3200 U/mg |
| Glycosylation: | non-glycosylated | and enzymatic mixtures containing that isoenzyme.

B) the peroxidase isoenzyme PT-S2 having the following characteristics:

| Natural Source: | Theobroma cacao |
|---|---|
| Location: | Extra-cellular |
| Mol. wt: | circa 36 kD |
| Optimum pH: | 5 to 6 |
| Haem Peak $\lambda_{max}$: | 419 nm |
| $R_2$: | 1.9 |
| pI: | >10 |
| Highest Specific Activity (Guaiacol): | 17800 U/mg |
| Highest Specific Activity (ABTS): | 3200 U/mg |
| Glycosylation: | not known, but probable | and enzymatic mixtures containing that isoenzyme.

C) the peroxidase isoenzyme PSA-S having the following characteristics:

| Natural Source: | Silene alba |
|---|---|
| Location: | Intra-cellular |
| Mol. wt: | circa 35 kD |
| Optimum pH: | 4.5 |
| Haem Peak $\lambda_{max}$: | 405 nm |
| $R_2$: | 3.8 |
| pI: | 9.5 |
| Highest Specific Activity (ABTS): | 7040 U/mg |
| Glycosylation: | not known | and enzymatic mixtures containing that isoenzyme,

The invention is further described and illustrated by the following experimental data.

EXPERIMENTAL DATA

1. Initiation and Maintenance of Cell Cultures

Cocoa cultures were initiated from pod tissue of *Theobroma cacao* on Murashige and Skoog[1] (M&S) agar medium supplemented with 1% (v/v) deproteinised coconut milk, 2 mg/L indole 3-burytic acid, 2 mg/L indole acetic acid and 0.1 mg/L kinetin. The carbon source was 2% (w/v) glucose and the pH of the medium was adjusted to 5.7 prior to sterilisation. When the culture was established, coconut milk was eliminated from the growth medium and the hormone combination changed to 1 mg/L indole 3-butyric acid and 0.5 mg/L zeatin. Two new cultures of *T. cacao* were initiated from this established cell line by direct, sterile transfer of inocula into different media. These new media contained 3% by weight total sugar as a source of carbohydrate, and also had a different hormone combination, viz: 1 mg/L 2,4-dichlorophenoxyacetic acid and 0.1 mg/L kinetin. The carbohydrate sources used were aqueous sugar solutions obtained by dissolving confectionery waste material supplied by courtesy of Trebor-Bassetts p.l.c. of Sheffield in water to give crude sugar solutions having the following analysis, based on total sugar content:

|  | Fructose | Glucose | Sucrose | Confectionery Source Material |
|---|---|---|---|---|
| Confectionery Waste No. 1 | 12% | 22% | 66% | Waste Jelly Babies |
| Confectionery Waste No. 2 | 2% | 9% | 89% | Waste Boiled Sweets |

*T. cacao* cultures were sub-cultured every 14 days by sterile transfer of 20 ml of culture into 100 ml fresh medium, in 250 ml Erlenmeyer flasks. The flasks are placed on a gyrotatory shaker at 150 rpm in the light at 25° C.

*Coleus blumei* cultures were set up from leaf tissue. The leaf callus was initiated on B5 agar medium (Gamborg et al[2]) containing the hormones 2,4-dichlorophenoxyacetic acid (1 mg/L), and kinetin (0.1 mg/L), with 2% (w/v) sucrose as the carbon source. The pH was adjusted to 5.8 prior to sterilisation. When established, the liquid suspension was sub-cultured by the sterile transfer of 16 ml of 7 day culture into 100 ml of fresh medium in 250 ml Erlenmeyer flasks. From this established suspension line, three new cultures were set up on a 10-day cycle, on media that differ only in the carbohydrate source used. One line continued with the original carbohydrate source, sucrose, whilst the other two use waste material from the confectionery industry, namely Confectionery Wastes 1 and 2 as above. These lines are maintained by sterile transfer of 20 ml of 10 day culture into 100 ml of fresh medium in 250 ml Erlenmeyer flasks. The flasks are placed on a gyrotatory shaker at 150 rpm in the light at 25° C.

To initiate *Silene alba* cultures, seeds were first sterilised and then germinated on sterile agar. Explants of the cotyledons were used to derive callus culture on B5 agar medium (Gamborg et al[2]) containing the hormones naphthalene acetic acid (NAA; 0.4 mg/L) and kinetin (0.04 mg/L), with 2% w/v sucrose. The pH of growth medium was adjusted to 5.8. Following initiation of the culture, a suspension culture was established on B5 medium (Gamborg et al[2]) containing the hormones NAA (1 mg/L) and kinetin (0.1 mg/L) and routinely sub-cultured by the aseptic transfer of 32 ml of 14 day old cells into 100 mL sterile medium in 250 mL Erlenmeyer flasks. The flasks are placed on a gyrotatory shaker at 150 rpm in the light at 25° C.

The three cultures referred to above were initiated in November 1984 (*C. blumei*), October 1986 (*T. cacao*) and June 1989 (*S. alba*) and have been routinely sub-cultured since then. Throughout that time the cultures have remained viable and have showed substantially constant levels of peroxidase production.

2. Growth Parameters

Fresh and dry weight measurements for all the *T. cacao* and *C. blumei* cultures were carried out according to the method described by Stepan-Sarkissian and Grey[3]. Examples of growth profiles of *T. cacao* and *C. blumei* on media containing pure sugars or confectionery waste are shown in the following figures.

Figure 2:
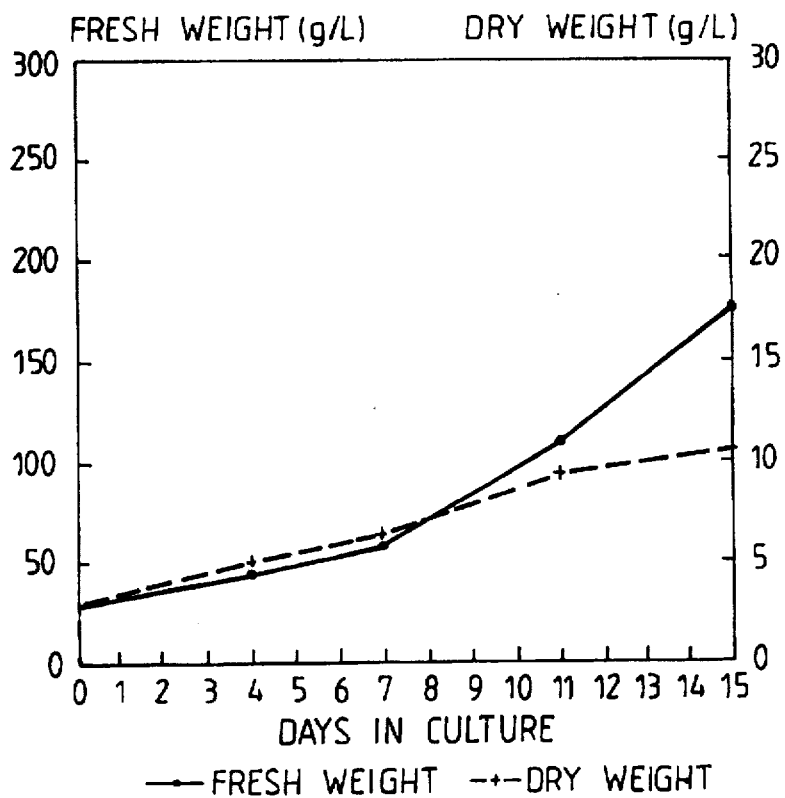
FIGS. 2 and 3 show the fresh and dry weights of the *T. cacao* growth cycle on two different confectionery wastes, Confectionery Wastes 1 and 2 respectively as the carbon source.
Figure 3:
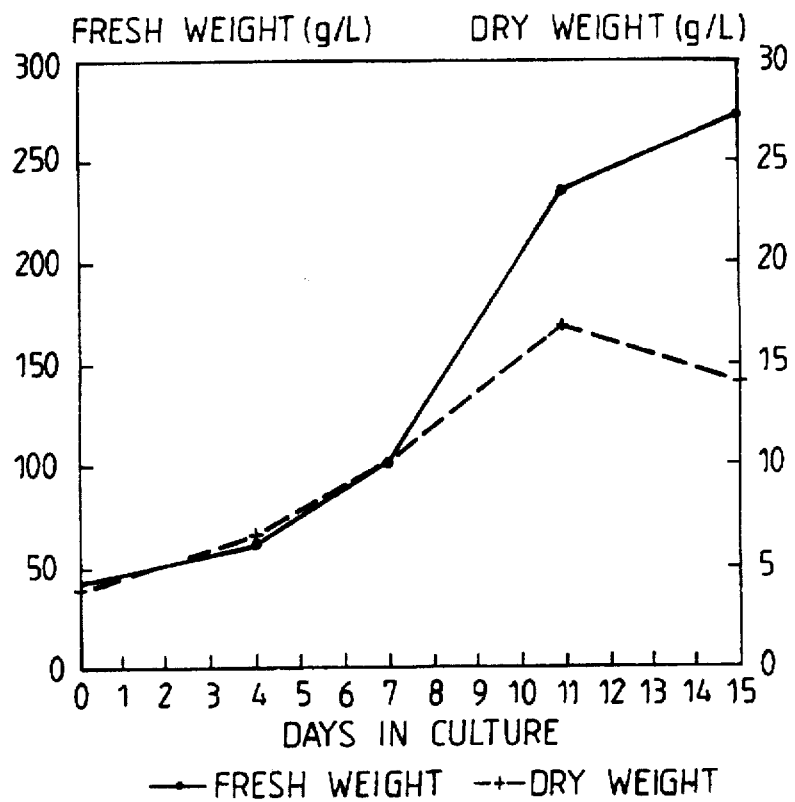

FIGS. 1 to 3 show typical growth profiles of each of the cocoa cell cultures on the three media described above. The cultures growing on confectionery waste (FIGS. 2 and 3) grow as well if not better than those grown on glucose (FIG. 1). Their best growth occurs on medium containing Confectionery Waste 2 (FIG. 3).

Figure 4:
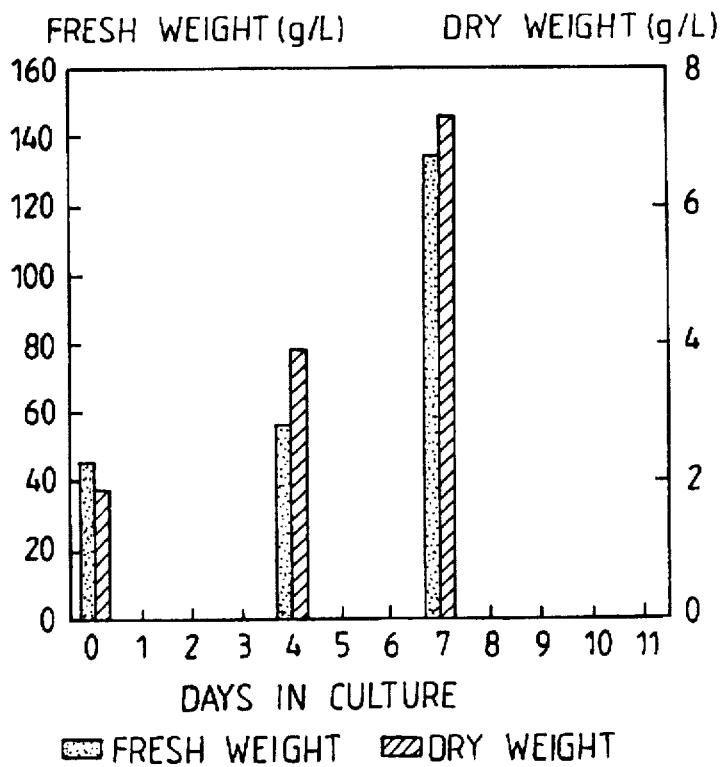
FIG. 4 shows the fresh and dry weights of *C. blumei* growth cycle, with sucrose as the carbon source.
Figure 5:
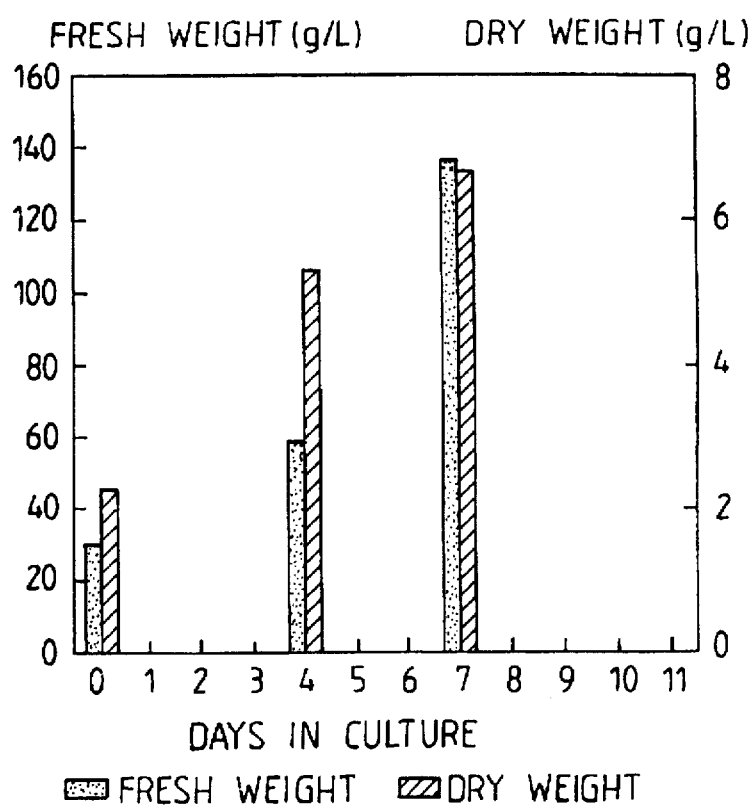
FIGS. 5 and 6 show the fresh and dry weights of the *C. blumei* growth cycle on the two different confectionery wastes, Confectionery Wastes 1 and 2 respectively as the carbon source.
Figure 6:
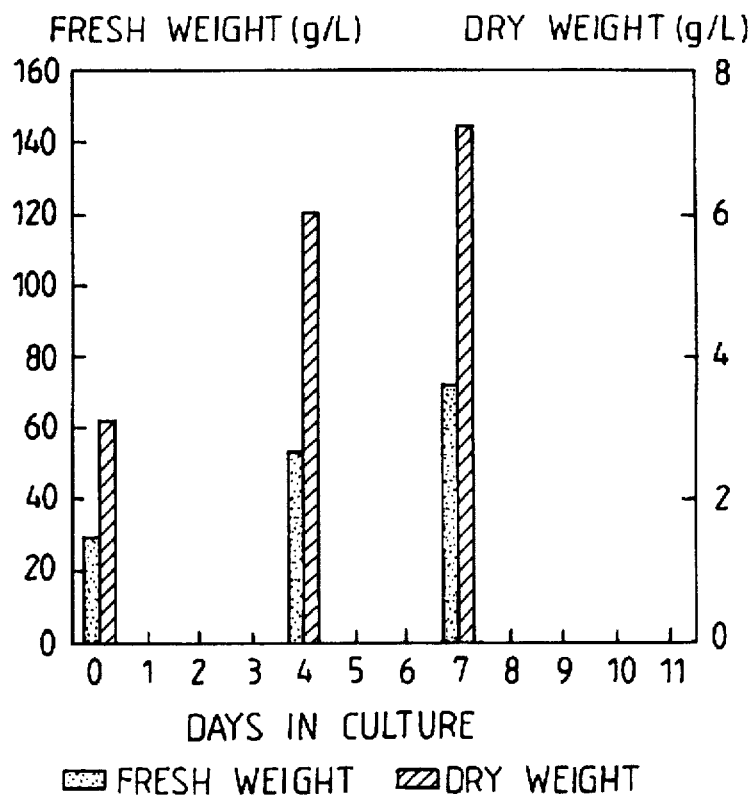

FIGS. 4 to 6 show examples of the growth patterns of the three *C. blumei* cultures described above. Again the growth rates are comparable on the different media, with growth on Confectionery Waste 2 (FIG. 6) being slightly slower than the other two media, sucrose (FIG. 4) and Confectionery Waste 1 (FIG. 5).

3. Estimation of Peroxidase Activity

In order to determine the percentage contribution of each fraction (cell and medium) to total culture activity, the peroxidase activity of the four cell lines was assessed both in the culture medium and in the cell mass. In the case of *T. cacao* and *C. blumei* the bulk of the peroxidase activity is extra-cellular. In the case of *S. alba* the bulk of the peroxidase activity is intra-cellular.

Preparation of cell extracts and medium allquots for the enzyme assay is carried out according to the procedure described by Grey[5]. The cells are disrupted on ice using a prechilled mortar and pestle with approximately 10% (w/v) prechilled, acid-washed sand and ice-cold 0.1M potassium phosphate buffer, pH 7.7. An Eppendorf system is used to centrifuge the cell homogenate for 2 minutes to remove sand and cell debris. The resulting supernatant is transferred to clean tubes and centrifuged for a further 5 minutes. The supernatant is carefully removed from the centrifuge tube and kept on ice before use.

Peroxidase catalyses a host of reactions in which hydrogen peroxide is a specific oxidising agent and a wide range of substrates act as electron donors.

$$H_2O_2 \cdot XH \rightarrow XOH + H_2O$$

The electron donors used in the assay described in this application are guaiacol, 2,2'-azino-bis(3-ethylbenzthiazoline-6-sulphonic acid) (ABTS), and 3,5,3',5'-tetramethylbenzidine hydrochloride (TMB).

a) Guaiacol $$H_2O_2 + 4 \text{ guaiacol} > H_2O_2 + \text{tetra-guaiacol}$$

| Enzyme assay | Medium (mL) | Cells (mL) |
|---|---|---|
| McIlvaine's citrate-phosphate buffer, pH 5.5 | 2.40 | 2.44 |
| 0.089M Guaiacol | 0.50 | 0.50 |
| 3.75M H$_2$O$_2$ | 0.04 | 0.04 |
| Cell extract | — | 0.02 |
| Medium | 0.06 | |

The reaction is initiated by the addition of hydrogen peroxide. The volume of cell extract is altered depending upon the activity of the enzyme, however the total assay volume is maintained at 3.0 mL by a corresponding change in the volume of buffer used. The appearance of tetraguaiacol, i.e. an increase in absorbence at 436 nm, is monitored during the initial reaction period at 25° C.

Peroxidase activity (Units/mL) in cell extract and medium was calculated according to the formula:

$$\frac{\Delta OD/\min \times 4 \times \text{reaction volume (mL)}}{25.5 \times \text{sample volume (mL)}} \quad \text{Equation 1}$$

where $\Delta OD/\min$ is the change in absorbence per minute at 436 nm, and the constant 25.5 is the molar extinction coefficient (cm$^2$/μmole) for tetraguaiacol. The constant 4 represents four moles of guaiacol necessary for the formation of one mole of tetra-guaiacol.

A unit of enzyme activity is defined as μmoles of substrate used per minute.

(b) 2,2'-Azino-bis(3-ethylbenzthiazoline-6-sulphonic acid) (ABTS)

| Assay mixture | |
|---|---|
| 13.6 mM ABTS in 0.1M KH$_2$PO$_4$ pH 5.0 | 2.90 ml |
| 0.236M H$_2$O$_2$ | 0.10 ml |
| Enzyme solution | 10–50 μl |

The enzyme is diluted according to its activity using a diluent solution consisting of 0.04M KH$_2$PO$_{4+}$, pH 6.8; 0.25% BSA; and 0.5% Triton X-100.

The change in optical density is followed at 405 nm and the change in OD is calculated over the linear section of the curve. There is a very slight background rate due to the reaction of $H_2O_2$ with ABTS, and $H_2O_2$ is therefore used to initiate the reaction. Under normal circumstances the background rate is negligible compared to the high activity of the samples. However if the activities are low a blank assay is included.

Peroxidase activity (Units/ml) in extracts is calculated according to the formula:

$$\frac{\Delta OD/\min \times \text{reaction volume}}{36.8 \times \text{sample volume}} \qquad \text{Equation 2}$$

where $\Delta OD/\min$ is the change in optical density per minute, and 36.8 is the molar extinction coefficient ($cm^2/\mu mole$) for the product of the reaction. A unit of enzyme activity is defined as $\mu$moles of substrate utilised per minute.

c) 3,5,3',5'-tetramethylbenzidine dihydrochloride (TMB)

Assay mixture 10 mg TMB dissolved in 10 ml 0.1M citric acid 70 ml d.$H_2O$ 20 ml 0.5M sodium acetate, containing 15.8 µl $H_2O_2$ Pipette 2.99 ml of the assay mixture into a cuvette.

Start the reaction with 10 µl enzyme.

The enzyme is diluted in d.$H_2O$ to a protein concentration of 0.1 to 1 µg/ml, depending upon activity.

The change in optical density is followed at 650 nm for 10 minutes and the change in OD/min is calculated over the linear section of the curve. After exactly 10 minutes, 0.5 ml 2M $H_2SO_4$ is added, and the change in OD at 450 nm is measured, to calculate the end-point.

Peroxidase activity (Units/ml) is expressed in terms of both the rate (at 650 nm) and the end-point (at 450 nm), according to the formulae:

$$\text{Rate} = \frac{\Delta OD_{650}/\min \times \text{reaction volume}}{39 \times \text{sample volume}} \qquad \text{Equation 3}$$

$$\text{End-point} = \frac{\Delta OD_{450}/\min \times \text{reaction volume}}{59 \times \text{sample volume}} \qquad \text{Equation 4}$$

where $\Delta OD/\min$ is the change in optical density per minute, 39 is the molar extinction coefficient ($cm^2/\mu mole$) for the intermediate product of the reaction, and 59 is the molar extinction coefficient ($cm^2/\mu mole$) for the end product. A unit of enzyme activity is defined as µmoles of substrate utilised per minute.

4. Production of Peroxidase by Cell Cultures

Figure 7:
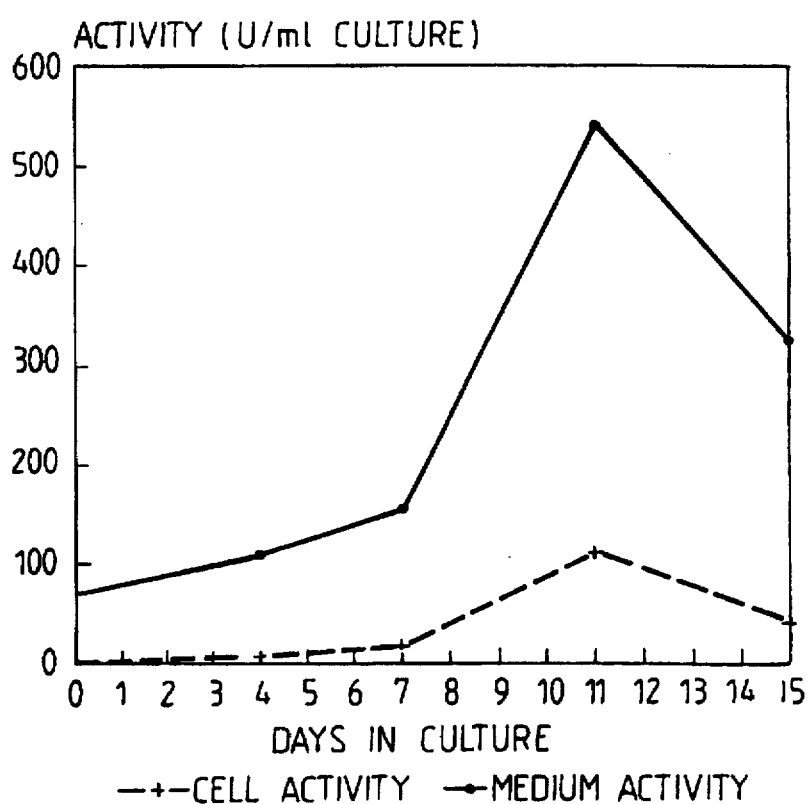
FIG. 7 shows the intra-cellular and extra-cellular peroxidase activity levels obtainable in cultures of *T. cacao* grown on glucose as a carbon source.
Figure 8:
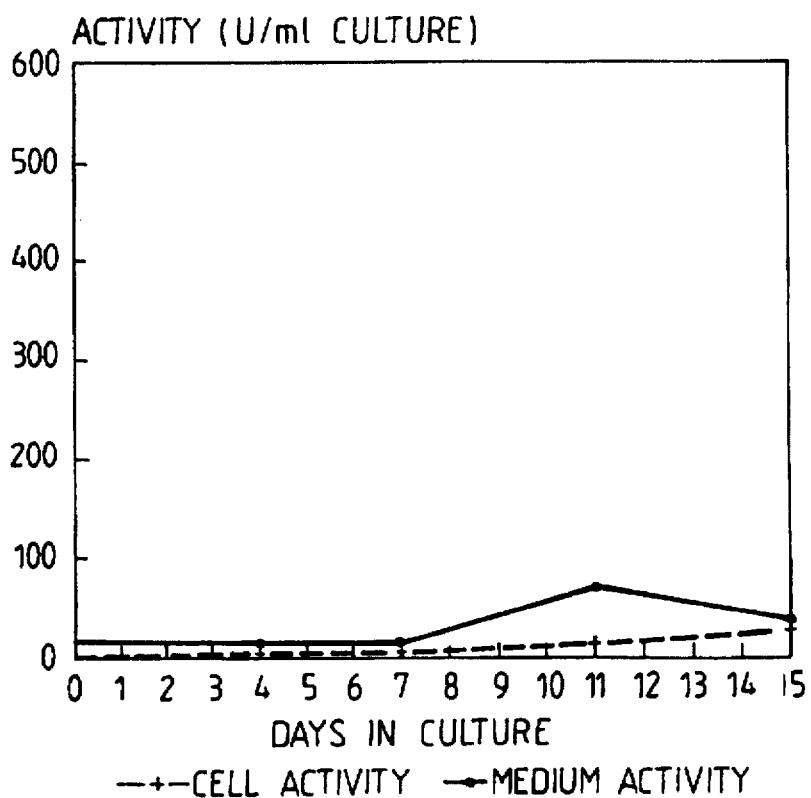
FIGS. 8 and 9 show the intra-cellular and extra-cellular peroxidase activity levels obtainable in cultures of *T. cacao* grown on the two different confectionery wastes, Confectionery Wastes 1 and 2 respectively as the carbon source.
Figure 9:
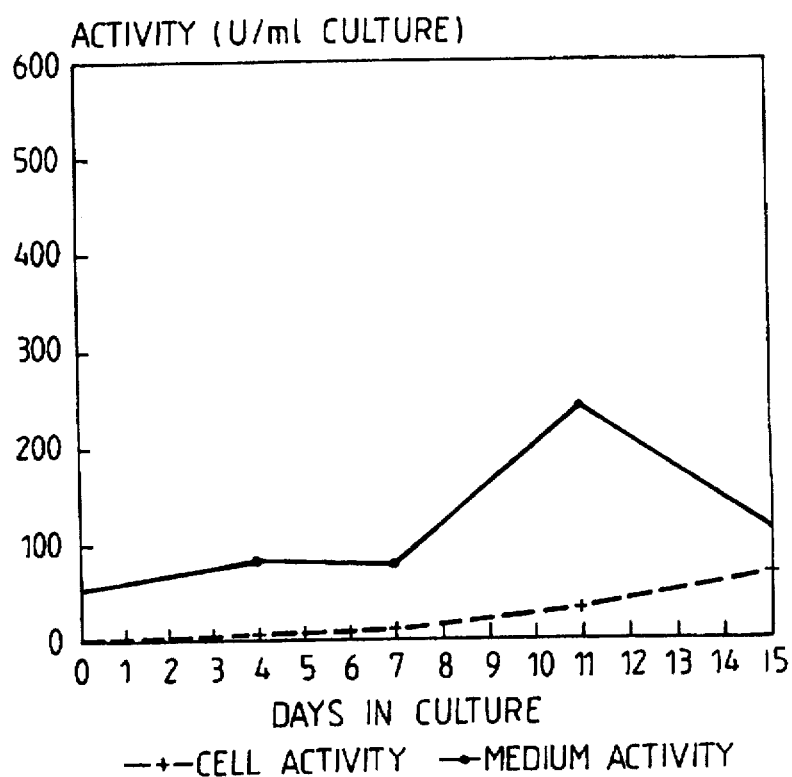

The production of peroxidase by *T. cacao* cultures was monitored using ABTS as a substrate (FIGS. 7 to 9). In all cases productivity peaked at day 11, and the bulk of the activity was found in the medium. The production of peroxidase was greater from glucose-grown cultures (FIG. 7) than those grown on confectionery wastes (FIGS. 8 and 9). Even cultures grown on Confectionery Waste 2 (FIG. 9), which grew substantially better than those grown on glucose, produced less than half the peroxidase. Nevertheless production was at a reasonable level on Confectionery Waste 2, and this substrate could be a viable alternative to glucose, given the less costly hormones used in the medium.

Figure 10:
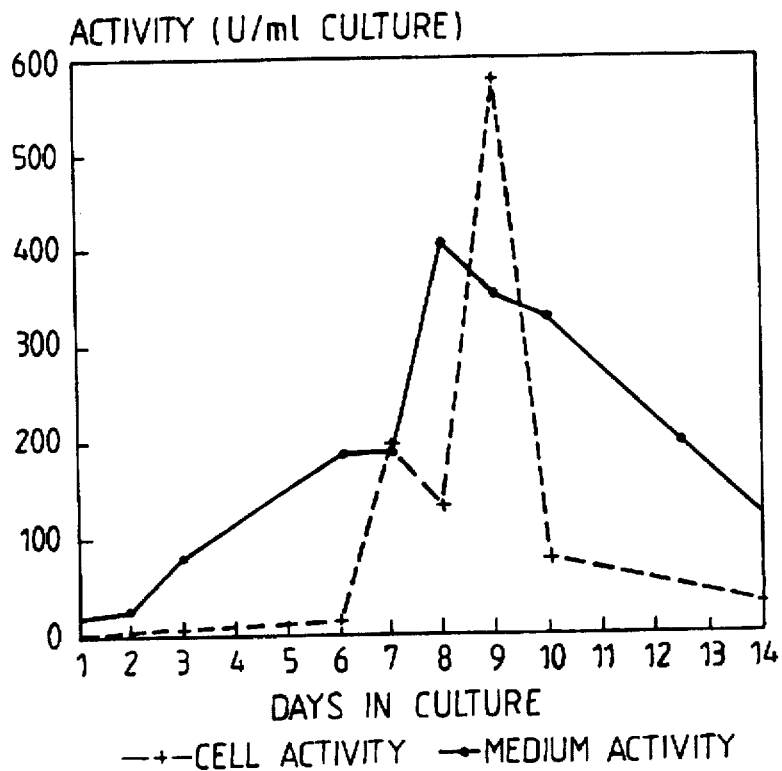
FIGS. 10 and 11 show the intra-cellular and extra-cellular peroxidase activity levels, assayed respectively with guaiacol and ABTS as substrates, obtainable in cultures of *C. blumei* grown on sucrose as a carbon source.
Figure 11:
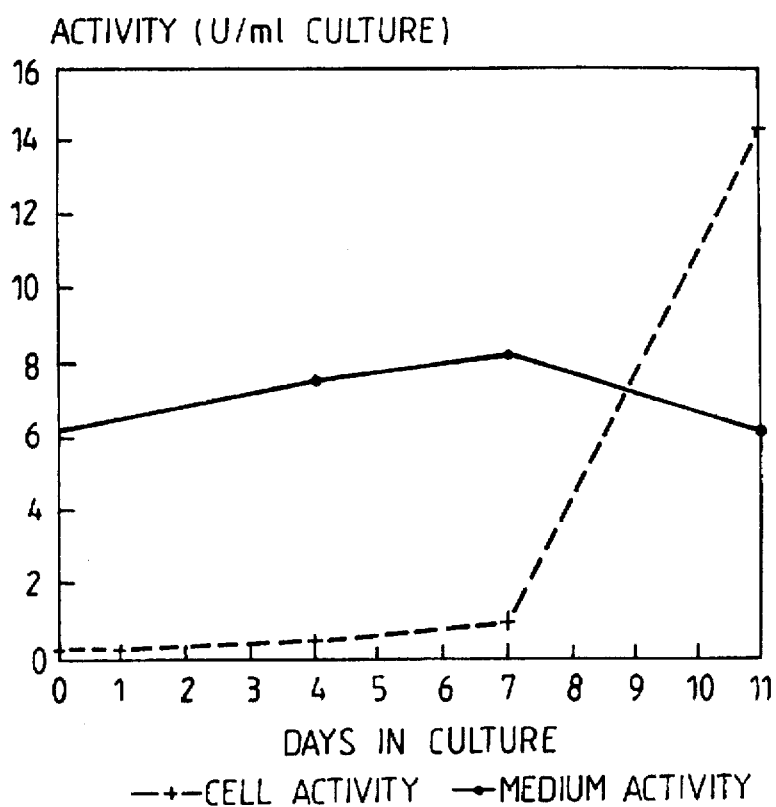
Figure 12:
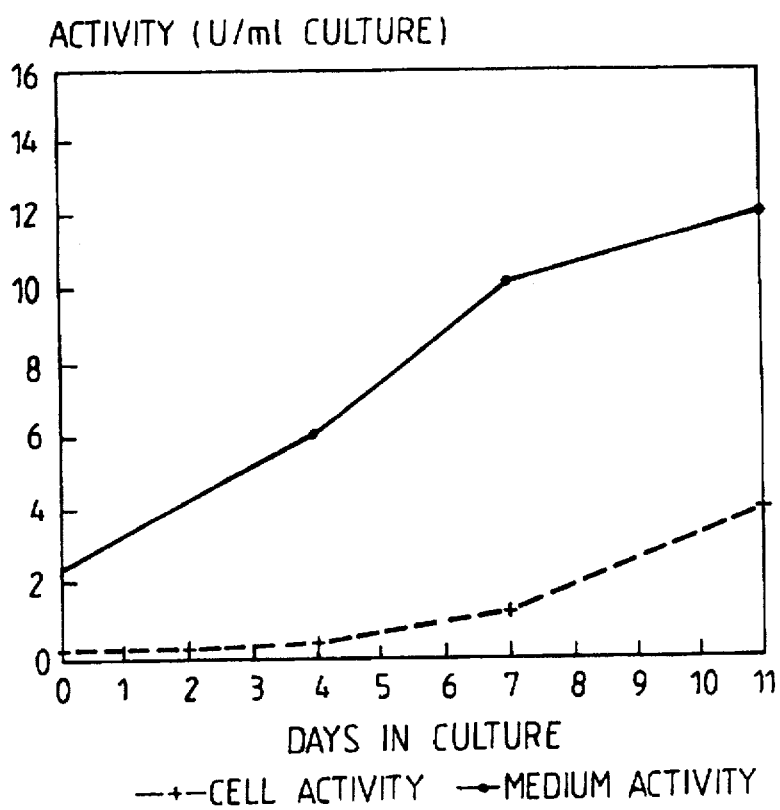
FIGS. 12 and 13 show the intra-cellular and extra-cellular peroxidase activity levels obtainable in cultures of *C. blumei* grown on the two different confectionery wastes, Confectionery Wastes 1 and 2 respectively as the carbon source.
Figure 13:
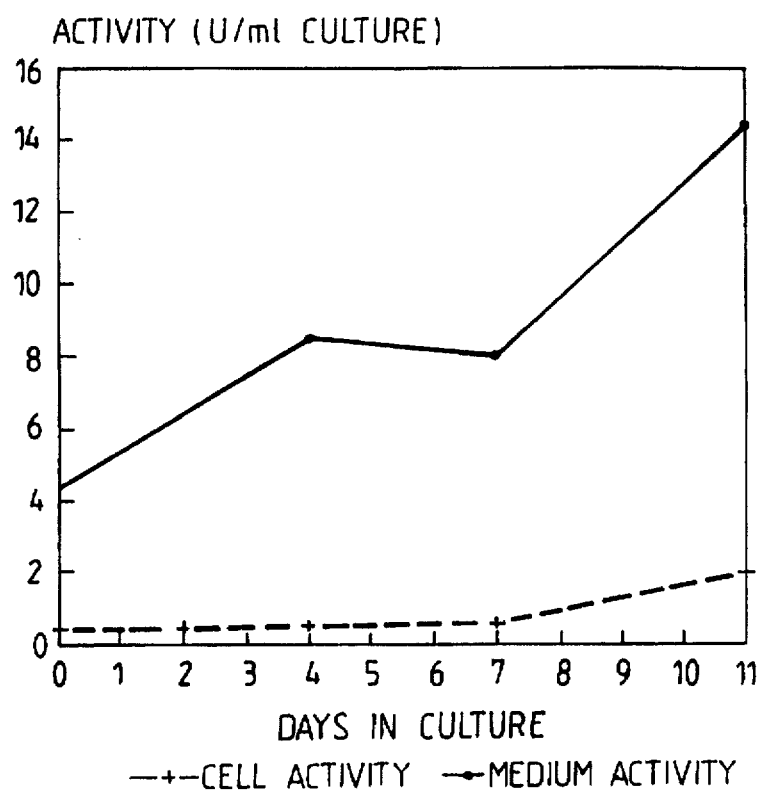

FIG. 10 shows the production of peroxidase by *C. blumei* cultures, as assayed with guaiacol as the enzyme substrate. The activity is found in the cells and the medium, with an activity peak at day 8 to 9. The production of peroxidase, assayed with ABTS, from cultures grown on different carbon sources is shown in FIGS. 11 to 13. Productivity is very similar in cultures grown on sucrose (FIG. 11) or confectionery waste (FIGS. 12 and 13), although the overall levels are low. The *C. blumei* peroxidase appears to have a much lower activity with ABTS than guaiacol.

High peroxidase activity (with ABTS) was found in *Silene alba* epicotyl-tissue-derived cell suspensions during a screen of various cell lines, and so was selected for further culture, purification and characterisation of that isoenzyme.

5. Characterisation of Crude Peroxidase Preparations

Peroxidase activity expressed in relation to units of volume of cell culture, or weight of cultured cells, is a useful means of assessing the productivity of a culture system, but to compare the activity of peroxidases from different sources the specific activity, or activity per mg protein, must be measured. For many commercial uses of peroxidase, particularly those that require the conjugation of the enzyme to a matrix or antibody, the specific activity of the enzyme is the important parameter. Furthermore measurements of specific activity are the only way of monitoring the purification of an enzyme.

One of the problems in measuring specific activity is that all methods of assaylug protein levels are influenced by the differing amino-acid compositions of the proteins being assessed. In crude mixtures of proteins these effects are balanced out, but as a protein becomes purer its difference from the average can become very marked, and this can affect the estimated specific activity by a factor of several fold. These factors must be borne in mind when assessing the data presented here on comparative specific activities. For some of the purer samples several different methods of estimating protein levels have been used in an attempt to provide some confidence limits on the comparisons being made.

For protein estimations of the crude peroxidase samples a commercial (Bio-rad, Hemel Hempstead, Hefts) Bradford test was used. The micro assay was used as the standard procedure. This involves adding 0.2 ml of the neat reagent to 0.8 ml of protein solution, diluted if necessary to give a concentration of 1 to 25µg/ml. In practice the range 5 to 15 µg/ml was found to be the most reliable, and all assays were performed in this range. The assay was standardised on BSA supplied as ampoules of a 2 mg/ml solution by Pierce (Rockford, Ill., USA). The reproducibility of the assays was monitored by including two quality controls in each run.

The specific activities of the crude peroxidase samples from cell culture media or cells were compared to that of a pure sample of horseradish peroxidase purchased from the Sigma Chemical Company, Poole, Dorset (Cat. No. P8375). Assaying the protein level in this sample presents a problem because, as a pure protein, it may differ considerably from the average. In practice two estimates have been used. First, as the protein was supplied pure in a pre-weighed amount, 3.9 mg, this value has been taken as the weight of the protein. Secondly the protein level has been assayed using the Bradford assay in exactly the same way as the crude peroxidase samples. Specific activities based on both assays have been quoted.

The enzyme assays were carried out as described in section 3, using guaiacot, ABTS, and TMB as substrates. Where necessary the samples were diluted with peroxidase diluent (0.04M potassium phosphate, pH 6.8; BSA, 0.25%;

Triton X-100, 0.5%), unless otherwise stated. The results are shown in Table 1.

TABLE 1

Peroxidase specific activities of crude preparations of *Theobroma cacao*, *Coleus blumei*, and *Silene alba* compared with pure *Amoracia rusticana* (horseradish) root peroxidase.

| Species | Specific activity (U/mg protein) | | |
|---|---|---|---|
| | ABTS | Guaiacol | TMB* |
| Crude *T. cacao* peroxidase (medium) | 3400 | 3740 | 1000 (800) |
| Crude *C. blumei* peroxidase (medium) | 490 | 16360 | 230 (130) |
| Crude *S. alba* peroxidase (cell) | 570 | n.d.** | 190 (250) |
| Pure *A. rusticana* peroxidase (wt) | 910 | 1760 | 980 (1090) |
| Pure *A. rusticana* peroxidase (Bradford) | 1820 | 3520 | 1960 (2180) |

*Calculated on the reaction rate at 650 nm. Figures in parentheses are based on the reaction end-point, determined at 450 nm.
**Not determined.

The *T. cacao* enzyme seems to have the highest specific activity with ABTS as substrate, and even in the crude form is substantially more active than the pure horseradish enzyme. The *C. blumei* enzyme is very active with guaiacol, but unfortunately this activity matched with the commercially more useful substrates, ABTS and TMB. This clearly illustrates the substrate-dependent nature of the enzyme activity, and shows that high activity with one substrate cannot be equated with high activity with any other substrate.

Figure 14:
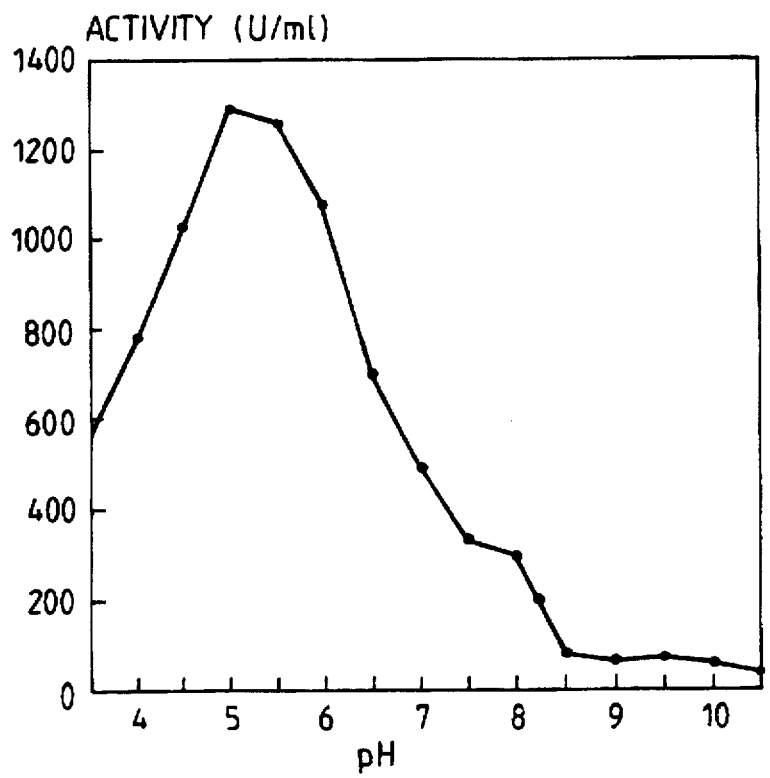
FIGS. 14 and 15 show respectively the pH profiles of the *T. cacao*, and *C. blumei* peroxidases, assayed with guaiacol as a substrate.
Figure 15:
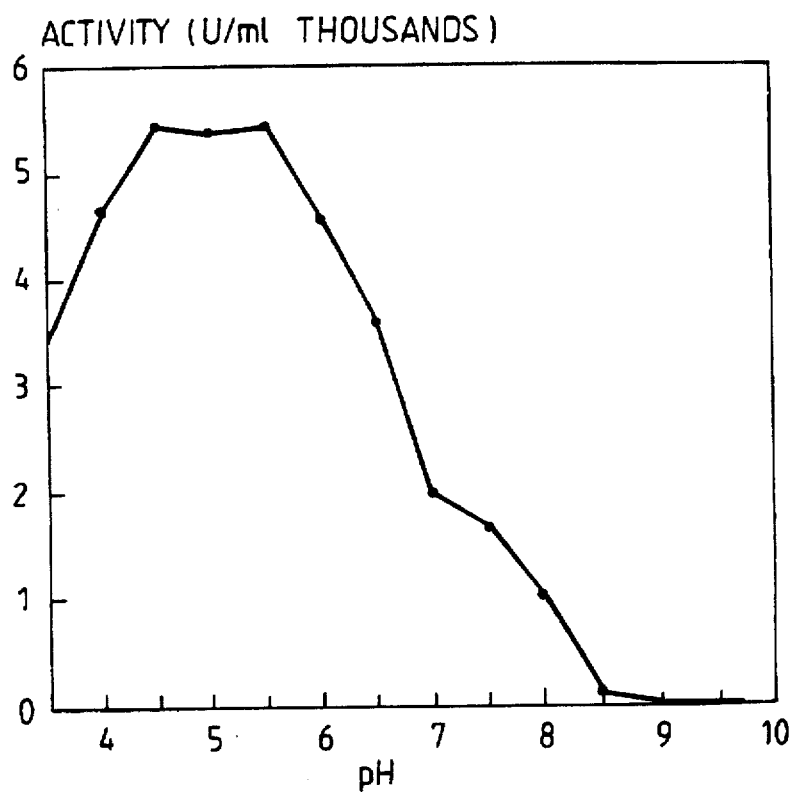
Figure 16:
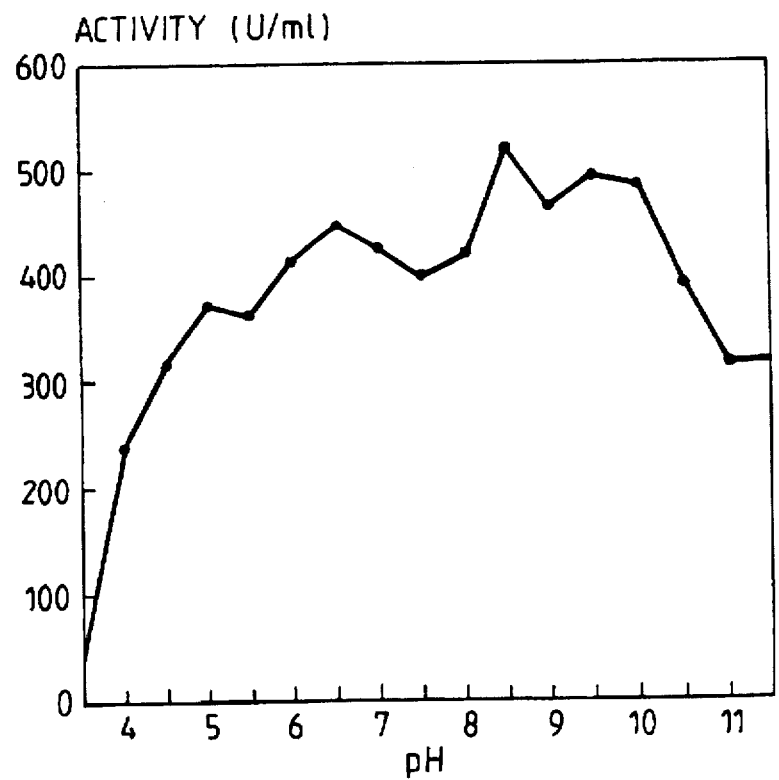
FIG. 16 shows the pH stability profile of the *C. blumei* peroxidase.

The pH optimum of the crude *T. cacao* peroxidase guaiacol activity is shown in FIG. 14. The optimum is around pH 5.0, and the peak is rather steep, with only 50% activity obtained at pHs 4.0 and 6.5. The *C. blumei* enzyme shows a similar optimum, although the peak in this case is rather less sharp (FIG. 15). The pH stability profile of the *C. blumei* enzyme shows a broad range of stability, with >50% activity retained from pH 4.0 to pH 11 (FIG. 16).

Stability studies on freeze-dried samples of the *T. cacao* and *C. blumei* enzymes suggest that the former is very stable at room temperature but for optimum stability the latter may require the addition of stabilisers and cryoprotectants, such as sucrose or trehalose. In accelerated stability tests crude freeze-dried *T. cacao* peroxidase has been stored at 37° C. for 2 months without loss of activity.

6. Purification of Peroxidases

Attempts have been made to purify the active peroxidases from the crude enzyme preparations. The primary objective of this was to isolate large enough samples of the various peroxidases to establish whether their properties are superior to the horseradish enzyme in terms of specific activity, stability and useful pH range. A secondary objective was to separate possible isoenzymes and investigate their individual characteristics. The criteria of purity are increased specific activity, appearance of a single band on SDS-PAGE, and the $R_z$ value (the ratio of the haem absorption peak at 403 nm to the protein absorption peak at 275 nm). The $R_z$ value of pure HRP is around 3.0.

(a) Purification of the *Theobroma Cacao* Peroxidase

Figure 17:
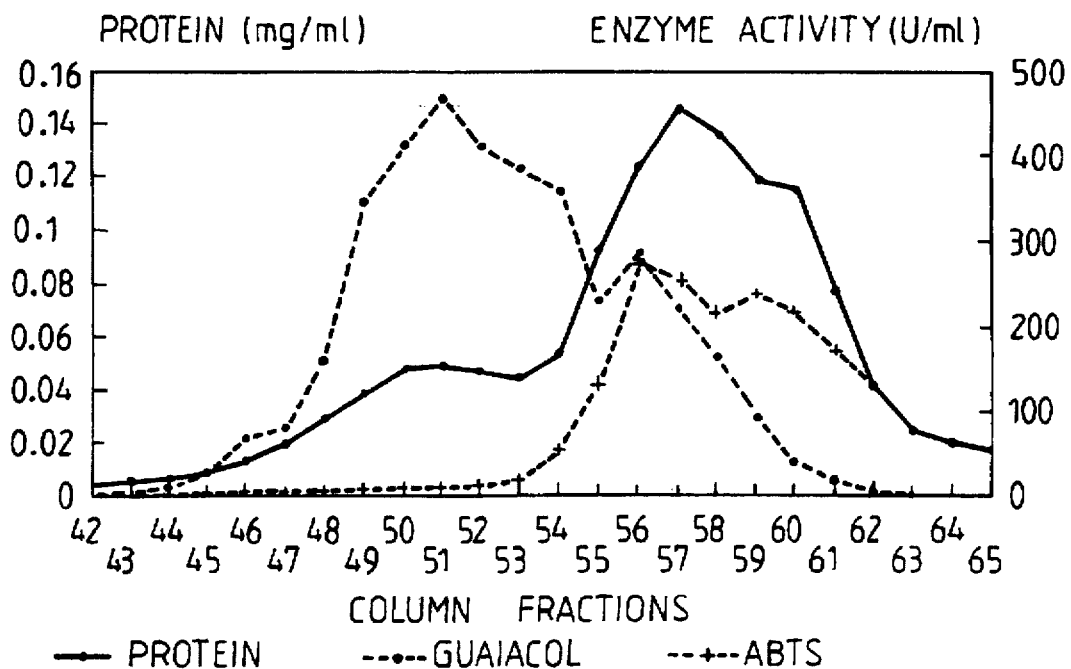
FIG. 17 shows the elution profile of the crude *T. cacao* peroxidase (from growth medium) separated on CM52.

The initial separation of the crude medium was carried out on a carboxymethyl cellulose column (CM52, Whatman, Maids tone, Kent). Medium (25 ml, containing approximately 7.Stag protein) was applied to a 50 ml CM52 column and eluted with a 0.01 to 0.6M gradient of sodium acetate, pH 5.0. Two cationic protein peaks were obtained, a small peak at 0.35M acetate (PT-CM1), and a large broad peak at (0.45M acetate (PT-CM2), see FIG. 17. In some runs the second peak separates into two, although SDS-PAGE gels show similar profiles for both peaks. Both PT-CM1 and PT-CM2 contained peroxidase activity, but PT-CM1 had a high specific activity for guaiacol and low for ABTS. Somewhat surprisingly, the reverse was true for PT-CM2. A small amount of peroxidase activity was also found in the antionic fraction, which comprised 30% of the total protein.

SDS-PAGE showed that PT-CM1 contained two polypeptides, of approximate molecular weight 36 kD and 41 kD, whereas PT-CM2 was much more complex with about 7 polypeptides, including a very prominent new band at 33 kD.

Figure 18:
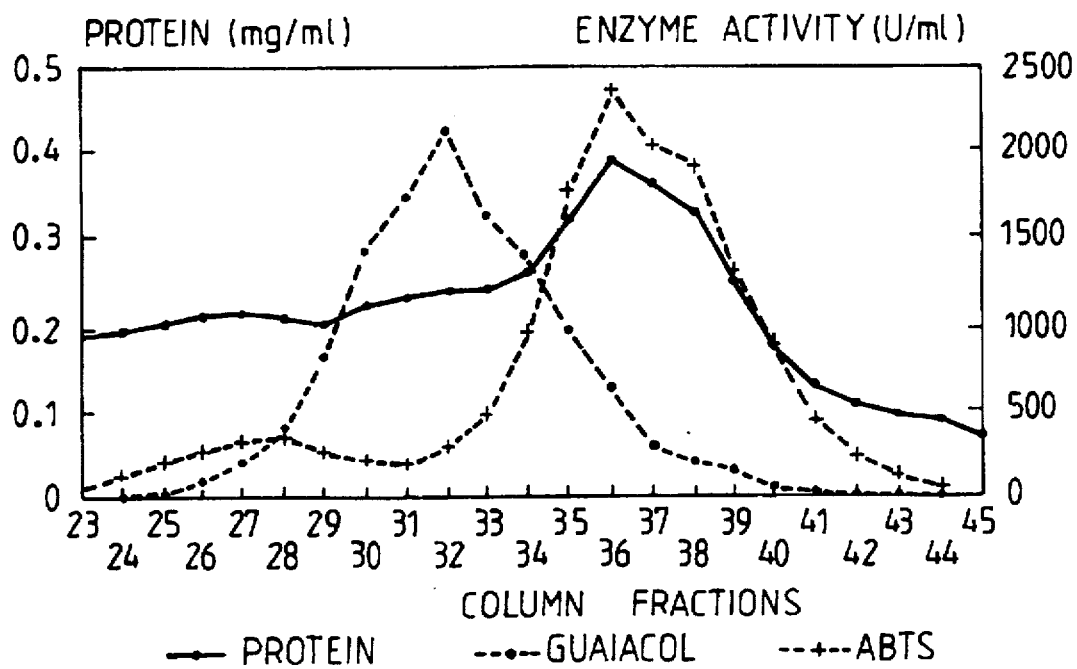
FIG. 18 shows the elution profile of the ABTS-specific *T. cacao* peroxidase fraction from CM52 (PT-CM2) further separated on Superose-12.
Figure 19:
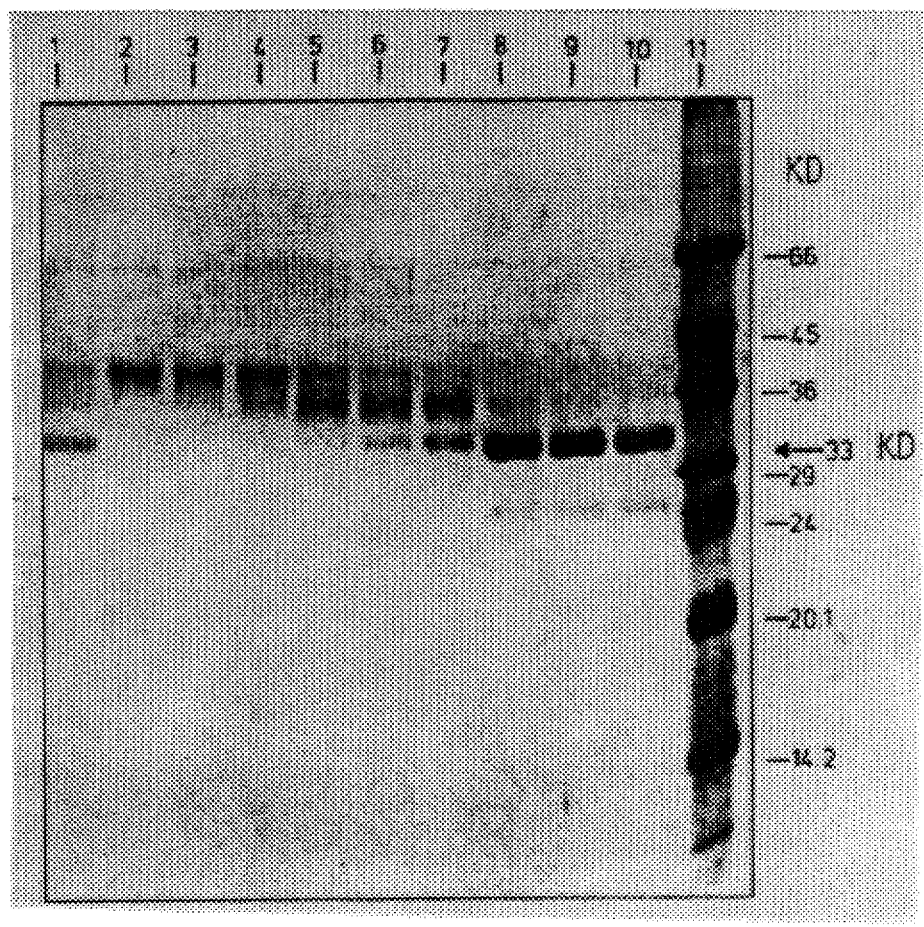
FIG. 19 shows an SDS-PAGE gel of the different *T. cacao* isoenzymes separated on Superose-12 and shows the three distinct bands at 33 kD for the three activity peaks.

PT-CM2 fractions were pooled (specific activity with ABTS, 3100 U/mg), concentrated in a Amicon concentrator (Amicon, Beverly, Mass.) and 100 µl containing 800 pg protein were loaded onto an FPLC (Pharmacia) Superose-12 column equilibrated in 0.1M sodium phosphate buffer, pH 7.5, 0.3M sodium chloride. Three peaks of peroxidase activity were obtained (FIG. 18) and correlation with SDS-PAGE gels suggested three isoenzyme types: an ABTS-specific enzyme of molecular weight 41 kD (PT-S1), a guaiacol-specific enzyme of 36 kD (PT-S2), and a non-glycosylated ABTS-specific enzyme of 33 kD (PT-S3) (FIG. 19). The latter was the predominant molecular species, and represented the bulk of the ABTS-specific activity. The molecular weight of PT-S3 is typical of the non-glycosylated chain of other plant peroxidases (e.g. HRPO) and suggests that the isoenzyme PT-S3 is in fact a non-glycosylation protein chain. This is confirmed by the fact that PT-S3 does not bind to Concavalin-A. Visual inspection of the SDS-PAGE gel suggested a purity of about 75%, and this also correlated with the value of 2.1. The amounts of protein obtained in this separation were too low to measure by the Bradford assay. Instead an estimate of the protein levels as made from the correlation of the $OD_{280}$ with the Bradford results on the PT-CM2 fractions. In addition calculations were made on the basis of the simple formula of 1 $OD_{280}$ unit=1 mg/ml protein of from the Warburg and Christian formula of $$1.55 \times OD_{280} - 0.76 \times OD_{260} = mg/ml\ protein$$

HRP was also assessed on the same basis. The results of the purification are summarised in Table 2, and the properties of the PT-S3 fraction are summarised in Table 3. Even on the most conservative estimation PT-S3 is considerably more active than pure horseradish peroxidase.

TABLE 2

Purification of *Theobroma cacao* peroxidase.

| Purification Step | Main molecular species | $R_2$ | Specific activity (U/mg protein) | |
|---|---|---|---|---|
| | | | ABTS | Guaiacol |
| Crude enzyme CM52 ion exchange | | | 3400 | 3740 |
| PT-CM1 | 41 kD, 36 kD | 1.6 | 240* | 9460* |
| PT-CM2 | 66, 41, 36, 33 kD | 1.3 | 2220* | 2300* |

TABLE 2-continued

Purification of *Theobroma cacao* peroxidase.

| Purification Step | Main molecular species | $R_2$ | Specific activity (U/mg protein) ABTS | Guaiacol |
|---|---|---|---|---|
| Pooled PT-CM2 Superose-12 | | | 3080 | 4080 |
| PT-S1 | 41 kD | n.d.** | 3300# | 3880# |
| PT-S2 | 36 kD | 1.9 | 2330# | 17800# |
| PT-S3 | 33 kD | 2.05 | 12050# | 3200# |

*Diluted in distilled water.
**Not determined.
Specific activity based on correlation between $OD_{280}$ and Bradford test.

TABLE 3

Properties of purified *T. cacao* peroxidase PT-S3 and *S. alba* peroxidase PSA-S.

| Property | PT-S3 | PSA-S | Pure HRP |
|---|---|---|---|
| Polypeptide molecular weight | circa 33,000 | circa 35,000 | circa 45,000 |
| Optimum pH | 4.5 | 4.5 | — |
| Haem Peak $\lambda_{max}$ | 403 nm | 405 nm | — |
| pI | >10 | 9.5 | 8.8 |
| $R_2$ | 2.05 | 3.8 | 2.8 |
| Specific Activity (ABTS): | | | |
| Bradford | 12046* (6.7 × HRP) | | 1800 |
| Weight | 12046* (13.2 × HRP) | | 910 |
| $OD_{280}$ | 4480 (2.3 × HRP) | 7040 (3.6 × HRP) | 1950 |
| $OD_{280}$ (W + C) | 5400 (2.4 × HRP) | 6880 (3.0 × HRP) | 2280 |

*Protein levels estimated from previously established correlation between $OD_{280}$ and the Bradford test for *T. cacao*.

One of the peroxidase substrates with commercial application is luminol, which is used in enhanced chemiluminescence (ECL) based detection kits, marketed by Amersham International. Fractions from the Superose-12 separation were tested for their activity with luminol in a simple dot-blot assay. The peak of luminol activity coincided exactly with the PT-S3 peak (the active ABTS peak), and the *T. cacao* enzyme was approximately 50% as active as the horseradish, if the protein levels of both were measured by $OD_{280}$.

The pI of the PT-S3 fraction was measured by iso-electric focusing, using a 'Phase' electrophoresis system (Pharmacia). The pI was >10 (the limit of detection).

Although systematic studies of the stability of the *T. cacao* have not been carried out, some evidence has been obtained that the enzyme is extremely stable. Samples of partially purified enzyme were stored in solution at 4° C. for over a year in either the sodium acetate buffer from ion-exchange chromatography, or phosphate buffer from gel filtration. Even after this time samples had remarkably high specific activities with ABTS. Three different ion-exchange samples had specific activities of 5000, 4800 and 4200 and two samples that had been further purified by gel filtration had specific activities of 3200 and 8400.

(b) Purification of the *C. blumei* Peroxidase

Figure 20:
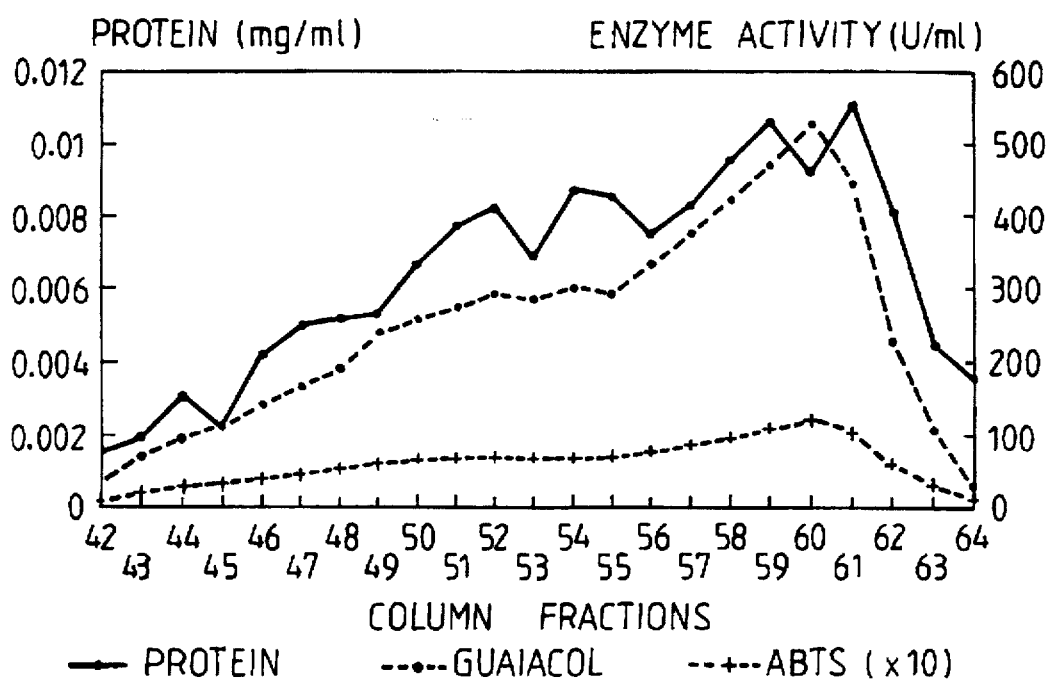
FIG. 20 shows the elution profile of the crude *C. blumei* peroxidase (from growth medium) separated on CM52.

Concentrated medium from *C. blumei* cell culture (25 ml, containing 3.7 mg protein and 45200 Units of peroxidase (guaiacol) was applied to an ion-exchange (CM52) column, as described for the *T. cacao* enzyme. 83% of the protein eluted in the anionic fraction, but only 27% of the guaiacol activity. The remainder eluted as a broad cationic peak, see FIG. 20. The ABTS activity followed the guaiacol activity, but was much lower: there was no evidence of isoenzymes with differing substrate specificities, as observed for *T. cacao*. The specific activity of the peak fraction, with guaiacol, was 57,300 U/mg, over 30 times that of pure horseradish peroxidase.

(c) Purification of Peroxidase from *Silene alba*

Figure 21:
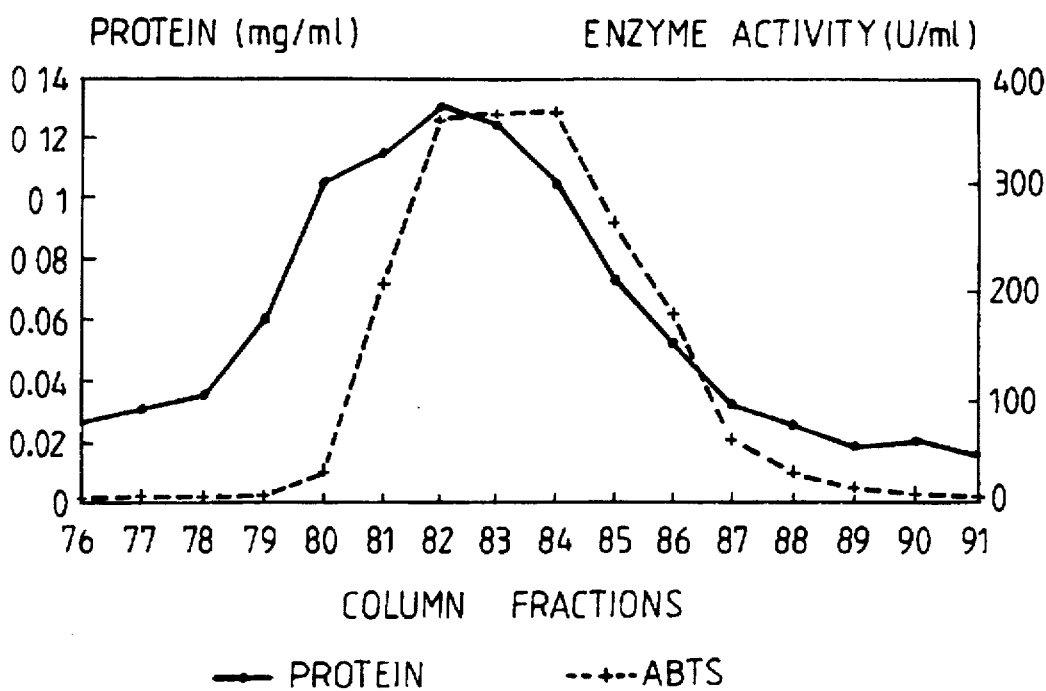
FIG. 21 shows the elution profile of the crude *S. alba* peroxidase (from cell extracts) separated on CM52.

A crude cell extract of *Silene alba* (30 ml, containing 16.6 mg protein and 9390 L2 of ABTS activity) was subjected to ion-exchange chromatography on CM-52, as described for the *T. cacao* extract. A large amount of protein, but very little peroxidase activity, was found in the anionic fraction, and there was a single peak of ABTS activity eluting in the cationic fraction at about 0.4M acetate (FIG. 21). This peak contained 23% of the protein applied, and 66% of the ABTS activity. The specific activity of the best fraction (PSA-CM) was 3550 U/mg, when the protein levels were measured by the Bradford assay. An SDS-PAGE gel of the peak fractions showed several polypeptide species, but a prominent band at about 35 kD correlated well with the activity profile.

Figure 22:
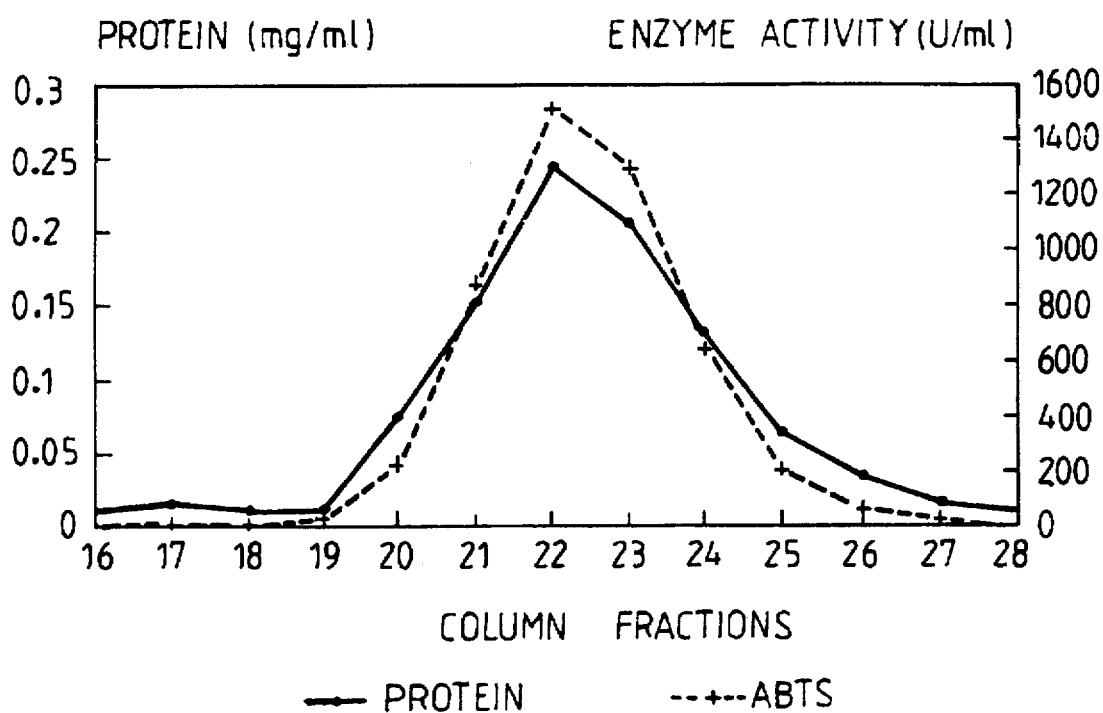
FIG. 22 shows the elution profile of the *S. alba* peroxidase fraction from CM52 (PT-CM2) further separated on Superose-12.
Figure 23:
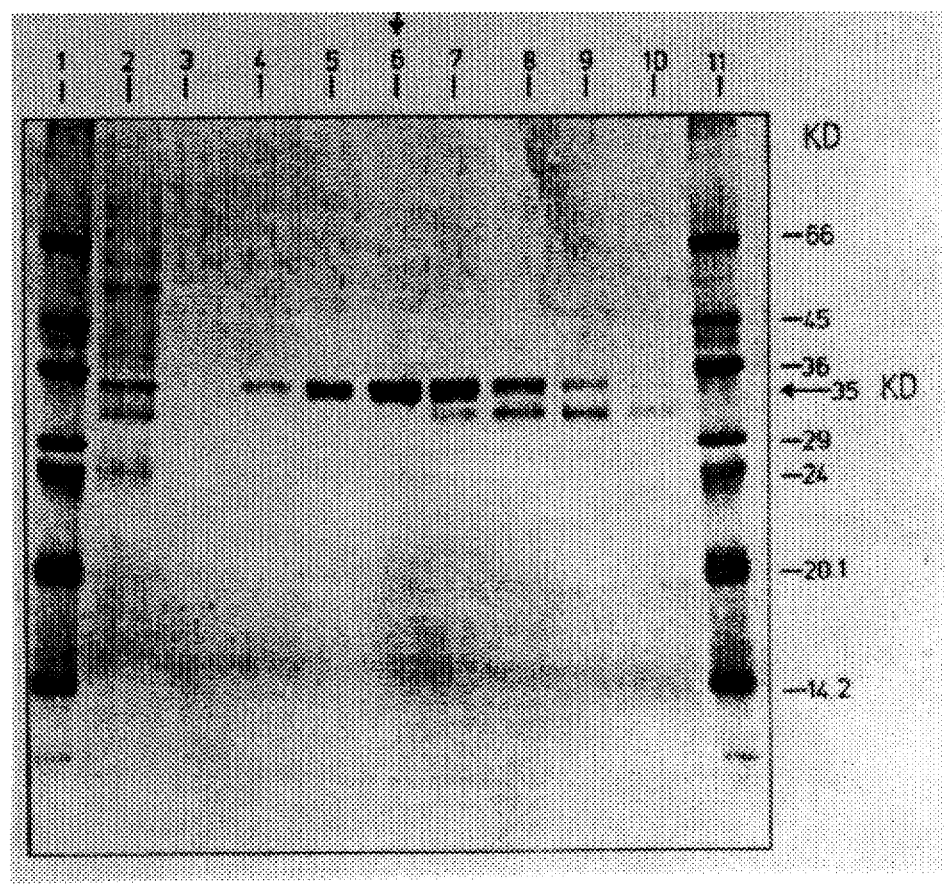
FIG. 23 shows an SDS-PAGE gel of the *S. alba* peroxidase purified on Superose-12 and shows by the arrows (column 6) the fraction (35 kD) having the highest specific activity.

Peak fractions were pooled and concentrated to 240.1 (5.3 mg/ml) in an Amicon concentrator. A sample (200 μl, 1.05 mg) was further separated on a Superrose-12 column as described for the *T. cacao* peroxidase. A single peak of peroxidase activity was obtained (PSA-S), with a specific activity (based on $OD_{280}$ measurements) of 7040 U/mg (FIG. 22). SDS-PAGE gels showed that about 80% of the peak fraction comprised the 35 kD polypeptide (FIG. 23). The properties of PSA-S are summarised in Table 3, and again this enzyme is considerably more active than horseradish peroxidase.

In conclusion, the above data demonstrates that the plant cell cultures of this invention are capable of producing high yields of peroxidase enzymes, all of which show superior properties to horseradish peroxidase, and in particular substantially improved specific activity levels.

References:

1. Murashige, T. & Skoog, F. (1962). Physiol. Plant., 15:473–497.
2. Gamborg, O. L., Miller, R. A. & Ojima, K. (1968). Exp. Cell Res., 50:151–158.
3. Stepan-Sarkissian, G. & Grey, D. (1990). Methods in Molecular Biology, volume 6, Plant Cell and Tissue Culture, Clifton, N.J., Humana Press, pp. 13–27.
4. Schripsema, J., Meijer, A. H., van Iren, F., ten Hoopen, H. J. G. & Verpoorte, R. (1990). Plant Cell Tissue Organ Cult., 22:55–64.
5. Grey, D. (1990). Methods in Molecular Biology, volume 6, Plant Cell and Tissue Culture, Clifton, N.J., Humana Press, pp. 555–562.

We claim:

1. A substantially purified peroxidase isoenzyme, wherein the isoenzyme is PT-S3, which is an unglycosylated, extracellular isoenzyme obtained from *Theobroma cacao*, having a molecular weight of about 33 kD, an optimum pH of 4.5, a haem peak of 403 nm, a $R_z$ of 2.05, a pI value greater than 10, a highest specific activity measured with 2,2'-azino-bis (3-ethylbenzthiazoline-6-sulfonic acid) of 12046 U/mg, and a highest specific activity measured with guaiacol of 3200 U/mg; and wherein the enzyme retains more than 33% activity after 1 year at 4° C. in sodium acetate or phosphate buffer.

2. A substantially purified peroxidase isoenzyme, wherein the isoenzyme is PT-S2, which is an extra-cellular isoenzyme obtained from *Theobroma cacao*, having a molecular weight of about 36 kD, an optimum pH between 5 and 6, a haem peak of 419 nm, a $R_z$ of 1.9, a pI value greater than 10, a highest specific activity measured with 2,2'-azino-bis(3-ethylbenzthiazoline-6-sulfonic acid) of 3200 U/mg, and a highest specific activity measured with guaiacol of 17800 U/mg.

3. A substantially purified peroxidase isoenzyme, wherein the isoenzyme is PSA-S, which is an extra-cellular isoenzyme obtained from *Silene alba*, having a molecular weight of about 35 kD, an optimum pH of 4.5, a haem peak of 405 nm, a $R_z$ of 3.8, a pI value of 9.5, and a highest specific activity measured with 2,2'-azino-bis(3-ethylbenzthiazoline-6-sulfonic acid) of 7040 u/mg.

\* \* \* \* \*